United States Patent [19]

Craig, Jr.

[11] Patent Number: 4,839,442

[45] Date of Patent: Jun. 13, 1989

[54] LOW VISCOSITY NONCRYSTALLINE DICYANATE ESTER BLENDS WITH PREPOLYMERS OF DICYANATE ESTERS

[75] Inventor: Wallace M. Craig, Jr., Fairdale, Ky.

[73] Assignee: Hi-Tek Polymers, Inc., Louisville, Ky.

[21] Appl. No.: 210,175

[22] Filed: Jun. 20, 1988

Related U.S. Application Data

[63] Continuation of Ser. No. 934,189, Nov. 24, 1986, abandoned.

[51] Int. Cl.[4] .............................................. C08G 73/00
[52] U.S. Cl. ..................................... 528/422; 560/301
[58] Field of Search ........................... 528/422; 560/301

[56] References Cited

U.S. PATENT DOCUMENTS

| | | | |
|---|---|---|---|
| 3,962,184 | 6/1976 | Notomi et al. | 528/422 |
| 3,987,230 | 3/1975 | Gaku et al. | 428/236 |
| 4,330,658 | 12/1980 | Ikeguchi | 528/73 |
| 4,709,008 | 11/1987 | Shimp | 528/422 |
| 4,740,584 | 4/1988 | Shimp | 528/422 |

FOREIGN PATENT DOCUMENTS 1305762  3/1970  United Kingdom .

*Primary Examiner*—Harold D. Anderson
*Attorney, Agent, or Firm*—Herbert P. Price

[57] ABSTRACT

Low viscosity dicyanate esters are made from bisphenols wherein the bridging member between the phenyl groups is unsymmetrical. These dicyanate esters are blended with prepolymers of dicyanate esters to form low viscosity non-crystallizing resins useful in preparing composites.

19 Claims, No Drawings

LOW VISCOSITY NONCRYSTALLINE DICYANATE ESTER BLENDS WITH PREPOLYMERS OF DICYANATE ESTERS

This is a continuation of co-pending application Ser. No. 934,189, filed on Nov. 24, 1986, now abandoned.

BACKGROUND OF INVENTION

The field of art to which this invention pertains is aryl cyanate esters, i.e., cyanic acid esters of polyhydric phenols.

Industry is constantly searching for lighter, stronger and more resistant materials to be used in place of the materials used today. For example, the aerospace industry is devoting considerable effort to utilizing structural composites in place of metals. Structural composites based on thermoplastic or thermoset resins and glass or carbon fibers have been and are being used successfully in many parts of military and commercial aircraft. Thermoset resins which are being used in such applications are epoxy resins, bismaleimide resins, and cyanate ester resins.

Cyanate ester resins, which are finding increasing use in structural composites, adhesives and electrical grade insulation are based on the reaction products of polyhydric phenols and cyanogen halides. Such resins and their methods of preparation are described in U.S. Pat. Nos. 3,403,128 and 3,755,042. Additional patents which describe cyanate esters are U.S. Pat. No. 3,987,230 and 4,330,658.

Such cyanate esters are generally crystalline in form but can be heated to form amorphous prepolymers which are partially trimerized resin intermediates. However, such homoprepolymers have a tendency to partially crystallize with time. Crystallized materials are difficult to handle in commercial operations and require extra heating to convert them to the amorphous form for ease of handling. Non-crystallizing homoprepolymers formed by increasing the degree of trimerization to 30 percent or greater have viscosities somewhat higher than prepreg manufacturers and fabricators of filament wound composites would like to use.

SUMMARY OF INVENTION

This invention relates to dicyanate ester compositions. In one aspect, this invention pertains to low viscosity cyanate esters based on bisphenols wherein the bridging member between the two phenyl groups is unsymmetrical. In another aspect, this invention relates to blends of the low viscosity cyanate esters and prepolymers of cyanate esters and to thermoset polymers obtained from the blends.

The low viscosity dicyanate esters of this invention have the structural formula:

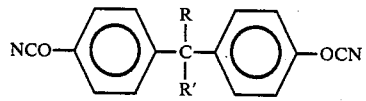

wherein R and R' are different and wherein R is H or $C_1$ to $C_3$ alkyl and R' is $C_1$ to $C_4$ alkyl. These dicyanate esters are non-crystalline and have viscosities of about 50 to about 2,000 cps at 25° C.

The low viscosity dicyanate esters of this invention can be blended with prepolymers of dicyanate esters of dihydric phenols to form fluid noncrystalline liquids.

When properly cured, the compositions of this invention produce thermoset plastics which have superior hot-wet mechanical properties (heat deflection temperature, flexure strength and flexural modulus) and low moisture absorption properties.

The compositions of this invention, particularly the blends, find uses in the formulation of tacky/drapable prepregs for structural composite end use, tacky/compliant structural film adhesives, filament winding resins, pultrusion resins, high solids coatings and electrical insulating (impregnating) varnishes, die-attach adhesives and reaction injection molding compounds.

DETAILED DESCRPTION OF INVENTION

The dicyanate esters useful in this invention are made by reacting a cyanogen halide with dihydric phenols in the presence of an acid acceptor, i.e., a base. This reaction is well known and is described in U.S. Pat. No. 3,755,402 which is hereby incorporated by reference. The cyanogen halides useful in this invention are cyanogen chloride and cyanogen bromide with cyanogen chloride being preferred.

The acid acceptors used to prepare dicyanate esters are inorganic or organic bases, such as sodium hydroxide, potassium hydroxide, sodium methylate, potassium methylate and various amines, preferably tertiary amines. Examples of useful amines are triethylamine, triproplyamine, diethylpropylamine, pyridine and the like. A preferred base is triethylamine.

The reaction is carried out in an organic solvent, such as ethylacetate, toluene, xylene, chlorinated hydrocarbons, acetone, diethylketone and the like. A preferred solvent is methylene chloride.

The reaction is conducted under low temperature conditions preferably between about $-30°$ C. and $0°$ C.

The dicyanate esters of this invention are made by reacting dihydric phenols with cyanogen halide using the procedure described in U.S. Pat. No. 3,755,402 referred to hereinabove. The dihydric phenols from which these dicyanate esters are prepared are bisphenols wherein the bridging member between the two phenyl groups is unsymmetrical. The formula for these dihydric phenols is

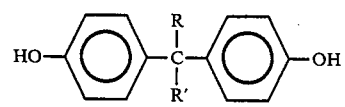

wherein each R is different and wherein R is H or $C_1$ to $C_3$ alkyl and R' is $C_1$ to $C_4$ alkyl. These dihydric phenols are derived from the condensation of phenol with acetaldehyde, methylethyl ketone, methylbutyl ketone, methyl-isobutyl ketone, methyl-t-butyl ketone, ethyl propyl ketone, ethyl-isopropyl ketone, propionaldehyde and butyraldehyde. The preferred dicyanate esters are those wherein R is hydrogen or methyl and wherein R' is methyl or ethyl.

The dicyanate esters of this invention are low viscosity noncrystalline liquids which have viscosities of about 50 to about 2000 cps at 25° C.

The viscosities of the dicyanate esters of this invention increase with time. However, the vicosities can be stabilized by the use of a small amount, generally about 0.01 to about 0.1 weight percent based on the weight of the dicyanate ester, of certain acids having a pKa below about 2. A preferred acid is p-toluene sulfonic acid.

Another effective class of stabilizer is polyphosphoric acid esters.

The dicyanate esters of this invention can be blended with other cyanate esters to form low viscosity blends which either do not crystallize or crystallize at a slower rate. Such other cyanate esters are made from the reaction of cyanogen halide with polyhydric phenols, such as resorcinol, bis(4-hydroxyphenyl) methane, bis(4-hydroxyphenyl)-2,2-propane (or Bisphenol A is it is commonly called), bis(4-hydroxyphenyl)ether, bis(4-hydroxphenyl)sulfide, bis(4-hydroxy-3,5-dimethylphenyl)methane, bis(4-hydroxy-3,5-dimethylphenyl)-2,2-propane, bis(4-hydroxy-3,5-dimethylphenyl)ether, bis(4-hydroxy-3,5,-dimethylphenyl) sulfide, 4,4'-(hexafluoroiso-propylidene)diphenol, p,p',p''-(trihydroxytriphenyl)ethane, dihydroxy-napthalene, novolak resins and the like.

Any amount of the low viscosity dicyanate esters of this invention can be blended with the other cyanate esters, e.g., 99 to 1 parts by weight to 1 to 99 parts by weight. Preferred blends are about 70 to about 95 parts by weight of the low viscosity dicyanate esters of this invention with about 30 to about 5 parts by weight, the total being 100 parts, of the dicyanate esters of bis(4-hydroxyphenyl)-2,2-propane or bis(4-hydroxy-3,5-dimethylphenyl) methane.

A particularly important aspect of this invention is the use of the low viscosity dicyanate esters to form blends with prepolymers of dicyanate esters.

Prepolymers are generally amorphous in form and possess an oligomeric physical state which is more suited for use in prepregging operations than the crystalline or semi-crystalline unpolymerized cyanate esters. Prepolymers are made by heating the dicyanate ester with or without catalyst at a temperature of about 140° C. to about 240° C. for a time sufficient to cyclotrimerize from about 5 to about 50 percent of the cyanate functional groups and, preferably, about 15 to about 40 percent of the cyanate functional groups. Useful prepolymers possess melt viscosities ranging from about 1,000 cps. at 50° C. up to 1,000,000 cps. Catalysts which can be used in preparing the prepolymers are mineral or Lewis acids, bases such as alkali metal hydroxides, alkali metal alcoholates or tertiary amines, salts such as sodium carbonate or lithium chloride, or active hydrogen containing compounds, such as bisphenols and monophenols. It is preferred to conduct the prepolymerization reaction with a catalyst, utilizing only heat followed by thermal quenching, in the manner taught by British Pat. No. 1,305,762 which is hereby incorporated by reference.

Cyanate ester content can be determined quantitatively by infrared analysis or by "residual heat of reaction" using a differential scanning calorimeter. The percent trimerization is calculated by the formula $$\text{Percent Trimerization} = 100 - \left[ \frac{\text{Wt/OCN Monomer}}{\text{Wt/OCN Prepolymer}} \times 100 \right]$$

wherein Wt/OCN is the equivalent weight per cyanate group.

Refractive index is directly related to the percent trimerization. A plot of refractive indices, taken at the same temperature, versus percent trimerization is linear. The slope of the plotted line will vary with the chemical composition of the particular cyanate ester or mixture being prepolymerized. By using these plots, the refractive index can be used to monitor the rate of reaction and the extent of the cyclotrimerization reaction.

Prepolymers can be made by homopolymerizing or copolymerizing the dicyanate esters described hereinbefore. Particularly preferred prepolymers are made by homopolymerizing the dicyanate ester of bis(4-hydroxyphenyl)-2,2-propane or bis(4-hydroxy-3,5-dimethylphenyl)methane, or by copolymerizing these dicyanate esters as described in commonly assigned application, Ser. No. 904,610, filed Sept. 8, 1986.

Blended compositions can be made with any amount of low viscosity dicyanate ester and prepolymer, e.g., 99 to 1 parts by weight of monomeric dicyanate ester to 1 to 99 parts by weight of prepolymer. Useful blends are made from about 5 to about 80 parts by weight of low viscosity dicyanate ester to about 95 to about 20 parts by weight of prepolymer.

The dicyanate ester-prepolymer blends of this invention are particularly useful in hot melt prepregging for aircraft structural composites and film adhesives. Hot melt prepregs are made by melting the prepolymer blends and applying it as a film to release paper. Unidirectional carbon fibers are laid down on the hot sticky film and another release paper is placed on top of the film and fibers. Resin impregnation of the fiber is achieved by hot-rolling the "sandwich". The prepreg is then stored under refrigeration. For use, the prepreg is thawed at room temperature, cut into required shapes, stripped of protective release paper and laid-up on molds for vacuum-bag curing. For large structural composites, e.g., tail structure of aircraft, up to a week may be needed to complete the lay-up. If the prepregs crystallize during this time, they will become stiff and boardy and will be difficult to conform to the desired shape. At least one week of freedom from crystallization at room temperature to 120° F., the temperature range in which prepregs are usually applied to the mold, is desired by structural composite manufacturers.

The prepolymer blends of this invention are non-crystallizing liquids and semisolids which are appreciably lower in viscosity at process temperatures in the range of 20° C. to 140° C. than are the unblended prepolymers.

The compositions of this invention in either unblended or blended form can be cured by heat alone but are preferably cured by the use of a catalyst plus heat. Such curing catalysts include those described above which are used in preparing prepolymers. Additional catalysts are those described in U.S. Pat. Nos. 3,962,184, 3,694,410 and 4,026,213 which are hereby incorporated by reference. Examples of such catalysts include zinc octoate, tin octoate, zinc stearate, tin stearate, copper acetylacetonate, phenol, catechol, triethylenediamine and chelates of iron, cobalt, zinc, copper, manganese and titanium with bidentate ligands such as catechol. Such catalysts are used in the amounts of about 0.001 to about 20 parts by weight per 100 parts by weight of the cyanate ester blend. A preferred catalyst system is that described in U.S. Pat. No. 4,604,452. Such catalysts are liquid solutions of a metal carboxylate and an alkylphenol, e.g., zinc napthenate and nonylphenol. These catalyst are used in the amounts of about 0.001 to about 0.5 part by weight of metal and about 1 to about 20 parts by weight of alkylphenol per 100 parts by weight of cyanate ester blend.

The compositions of this invention are cured by heating at elevated temperatures for a time sufficient to obtain a complete cure, i.e., until at least about 80 percent of the cyanate functional groups are cyclotrimerized. The curing reaction can be conducted at one temperature or can be conducted by heating in steps. If conducted at one temperature, the temperature will vary from about 250° F. to about 450° F. When conducted by stepwise heating, the first step, or gelation step, is performed at a temperature of about 150° F. to about 350° F. The curing step is conducted at a temperature of about 300° F. to about 450° F., and the optional post-curing step is conducted at a temperature of about 400° F. to about 550° F. The overall curing reaction will take about 5 minutes to about 8 hours.

The dicyanate ester blends and co-prepolymers of this invention can be blended with polyepoxide resins and can be cured to form useful thermoset compositions. Up to about 70 weight percent based on total blend weight can be polyepoxide resin. Such polyepoxide resins are the well-known glycidyl ethers of polyhydric phenols which are made by reacting an epihalohydrin, preferably epichlorohydrin, with a polyhydric phenol, preferably Bisphenol A.

When formulating for particular end uses, additional components can be incorporated in the polycyanate composition. Such components include minor amounts of thermoplastic resin tougheners, reinforcing fibers, colloidal silica flow modifiers, mineral fillers and pigments.

The cured compositions of this invention can be used in vacuum bagged structural composites, transfer molded encapsulants, filmed structural adhesives, printed wiring boards and composites for aircraft primary structures.

The following examples will describe the invention in more detail. Parts and percentages unless otherwise indicated are parts and percentages by weight. BADCy referred to in the examples is bis(4-cyanatophenyl)-2,2-propane. METHYLCy is bis(4-cyanato-3,5-dimethylphenyl)methane. BEDCy is bis(4-cyanatophenyl)-1,1-ethane. MEKCy is bis(4-cyanatophenyl)-2,2-butane.

EXAMPLE 1

Synthesis of bis(4-cyanatophenyl)-2,2-butane (MEKCy)

To a suitable reactor were added 700 parts of methylene chloride. Cyanogen chloride, 127.3 parts, was then added by a sparge over a one hour and twelve minor period with the temperature being held at 1° C. to 7° C. A solution of 245.5 parts of bis(4-hydroxyphenyl)-2,2-butane in 255 parts of acetone was added over a 13 minute period with the temperature being held at 2° C. to 8.5° C. The temperature was then lowered to −10° C. and 204.9 parts of triethylamine were added over a 40 minute period while holding the temperature at −10° C. The reactants were then washed with 600 parts of water followed by a wash with 900 parts of water and then with 2 washes using 1000 parts of water in each wash. When the washing was completed, the organic solvent solution of the product was vacuum distilled to remove volatiles to a pot temperature of 71° C. and a full vacuum of 30 inches mercury pressure. A liquid dicyanate ester product was recovered in the amount of 288.5 parts having a viscosity of U (Gardner-Holdt at 25° C.), equivalent to about 630 cps, and a Gardner color of 4 to 5.

To 140 parts of the dicyanate ester was added a solution of 0.07 part of p-toluene sulfonic acid in 0.09 part of methylethyl ketone. The resulting blend (Blend A) was poured into a viscosity tube which was sealed and then placed in a hot box at 50° C. A portion of the dicyanate ester which did not contain the paratoluene sulfonic acid (Blend B) was poured into another viscosity tube which was sealed and also placed in a hot box. The viscosities were then measured over a 12 week period, with the following results:

| Time at 50° C. | Gardner-Holdt Viscosity at 25° C. | |
| --- | --- | --- |
| | Blend A | Blend B |
| Initial Viscosity | U | U |
| 1 week | U | Y− |
| 3 weeks | V− | >$Z_7$ |
| 5 weeks | W | >>$Z_7$* |
| 6 weeks | X | >>$Z_7$* |
| 12 weeks | Z,** | Solidified |

*Solidified in bottom half
**Solidified in bottom third

EXAMPLE 2

The dicyanate esters described in Example 1, both stabilized (Blend A) and unstabilized (Blend B), were deaired under vacuum. To 125 parts of each ester was added a catalyst blend of 2.5 parts of nonylphenol and 0.156 parts of zinc naphthenate containing 8 percent zinc as metal. The catalyzed cyanate esters were then poured into aluminium sheet molds preheated at 200° F. The molds were then heated at 200° F. or at 220° F. until the resins were gelled. The gelled resins were then cured by heating for one hour at 350° F., one hour at 420° F., and two hours at 482° F. The resulting castings, ⅛ inch thick, were sawed and milled into test bars which were subjected to physical testing. The results of these tests were as follows:

| Resin | Blend A | Blend B |
| --- | --- | --- |
| Gel time | 107 min. | 124 min. |
| Temp. | 220° F. | 220° F. |
| Heat Distortion Temp °C. | | |
| Dry | 247 | 248 |
| Wet* | 205 | 210 |
| % $H_2O$ Absorption* | 1.15 | 1.19 |
| Flexural Strength, psi | 21,000 | 19,100 |
| Flexural Modulus, ($10^6$ psi) | 0.40 | 0.38 |
| Flexural Strain (percent) | 5.75 | 5.72 |

*Test bars conditioned 64 hours at 200° F. and >95 percent R.H. prior to testing.

EXAMPLE 3

To a suitable reactor where added 1050 parts of methylene chloride. Cyanogen chloride, 143.3 parts, was then added by means of a sparge over a one hour and 52 minute period while keeping the temperature between 1.5° and 6.8° C. The temperature was then lowered to 2.6° C., and a solution of 276.4 parts of bis(4-hydroxyphenyl)-2,2-butane in 300 parts of acetone was added over a 12 minute period with the temperature rising to 8.1° C. The temperature was then lowered to −10° C. and 230.73 parts of triethylamine were added over a 40 minute period while keeping the temperature at −10° C. during the addition. The reaction product was then washed with 1000 parts of water. The washing was repeated three times. When the washing was completed, distillation of the organic solvent solution was begun to remove volatiles. When the pot temperature reached 46° C., a solution of 0.1685 part of p-toluene sulfonic acid dissolved in 0.5 part of methylethyl ketone was added. Heating was continued to remove volatiles. When the pot temperature reached 60° C., vacuum was applied. Vacuum distillation under full vacuum (29.5 inches mercury pressure) was continued, to a pot temperature of 73° C. The dicyanate ester product was recovered in the amount of 342 parts.

The MEKCy product was blended with BADCy and with METHYLCy and the blends were heated in an oil bath until clear and homogeneous. The blends were then poured into viscosity tubes which were sealed and left at room temperature overnight. The viscosity tubes were then placed in a 50° C. hot box and were monitored for crystal formation and viscosity. All viscosity measurements were made at 25° C. The amounts of each component and the results of the crystal formation and viscosity monitoring are found in the following table:

|  | A | B | C | D | E | F |
|---|---|---|---|---|---|---|
| Components (parts) | | | | | | |
| MEKCy | 13.5 | 10.5 | 7.5 | 13.5 | 10.5 | 7.5 |
| BADCy | 1.5 | 4.5 | 7.5 | — | — | — |
| MethylCy | — | — | — | 1.5 | 4.5 | 7.5 |
| Crystal Formation and Gardner-Holdt Viscosity | | | | | | |
| Overnight | None | None | 1 hrs | None | 3 hrs | 10 mins. |
| Init Visc | Q | M-N | — | T-U | — | — |
| 1 week - 50° C. | Q | M-N | | T-U | | |
| 1 week RT | clear liquid | clear liquid | | clear liquid | | |
| 2 weeks - 50° C. | Q | M-N | | T-U | | |
| 2 weeks RT | | same as 1 week | | | | |
| 8 weeks - 50° C. | U-V | U | | W | | |
| 8 weeks RT | | same as 1 week | | | | |

EXAMPLE 4

Using the same procedure described in Example 1, the dicyanate ester of bis(4-hydroxyphenyl)-1,1-ethane was prepared by reacting 207.2 parts of the bisphenol with 121 parts of cyanogen chloride and 195.75 parts of triethyl amine in 700 parts of methylene chloride and 250 parts of acetone. The dicyanate ester was stabilized after washing with 0.1293 part of p-toluene sulfonic acid in 0.5 parts of methylethyl ketone. The product was recovered in the amount of 252 parts and had an initial Gardner-Holdt viscosity at 25° C. of B+. After one week at 50° C. the viscosity was still B+ (about 70 centipoises).

To 125 parts of the dicyanate ester was added a solution of 0.156 part of zinc naphthenate (8 percent zinc as metal) dissolved in 2.5 parts of nonylphenol. The curable composition was poured into an aluminum mold preheated to 200° F. The mold was heated for one hour at 200° F. and 173 minutes at 220° F. to gel the composition. The composition was then heated for one hour at 350° C., one hour at 420° F. and two hours at 482° F. The physical properties of the resulting casting are listed below:

| Heat Distortion Temp. | |
|---|---|
| Dry °C. | 220 |
| Wet °C.* | 185 |
| Percent $H_2O$ absorption* | 1.23 |
| Flexure Strength (psi) at 25° C. | 21,900 |
| Flexure Strain at break (%) 25° C. | 6.14 |
| Flexure Modulus ($10^6$ psi) at 25° C. | 0.40 |
| Flexure Strength (psi) at 325° F. (Dry) | 7,500 |
| Flexure Strain at break (%) at 325° F. (Dry) | >13.8 |
| Flexure Modulus ($10^6$ psi) at 325° F. (Dry) | 0.12 |
| Flexure Strength (psi) at 325° F. (Wet)** | 3,100 |
| Flexure Strain at break (%) at 325° F. (Wet)** | >13.8 |
| Flexure Modulus ($10^6$ psi) at 325° F. (Wet)** | 0.08 |

*Test bars conditioned 64 hours at 200° F. and >95 R.H. prior to testing.
**Flexure bars conditioned 48 hours in boiling water prior to testing.

EXAMPLE 5

A prepolymer (Prepolymer 1) was prepared by reacting 50 parts of METHYLCy with 50 parts of BADCy at 210° C. until the refractive index at 110° C. was 1.5427, indicating 21 percent trimerization. The prepolymer had a viscosity of 55,200 cps at 77° F.

Another prepolymer (Prepolymer 2) was prepared by reacting 100 parts of BADCy at 190° C. until the refractive index at 110° C. was 1.5622, indicating 31.5 percent trimerization. The viscosity of Prepolymer 2 was 5,200,000 cps at 77° F.

Prepolymer 1 and Prepolymer 2 were blended with various amounts of BEDCy (Example 4 dicyanate ester) and the viscosity of the blends at 25° C. was determined. The blends were then poured into viscosity tubes, the tubes were sealed and placed in a hot box at 50° C. The viscosity of the blends after aging at 50° C. was determined over a period of time. The crystallization development at room temperature and at 50° C. was also determined.

Prepolymer 1 and Prepolymer 2 were also blended with BADCy monomer. The blends crystallized before viscosities could be determined.

The viscosities (measured at 25° C.) and crystallization tendencies are listed in the following table:

| Components | A | B | C | D | E | F |
|---|---|---|---|---|---|---|
| BEDCy | 6.0 | 10.0 | 14.0 | 12.0 | 8.0 | 15.0 |
| PREPOLYMER 1 | 14.0 | 10.0 | 6.0 | — | — | — |
| PREPOLYMER 2 | — | — | — | 8.0 | 12.0 | 5.0 |
| Init. Visc. (cps) | 10,900 | 1860 | 500 | 1560 | 9750 | 475 |
| 1 wk at 50° C. | $Z_6$+ | $Z_1$ | T-U | Z | $Z_6$ | U |
| 1 wk at R.T. | | | No crystals | | | |
| 2 wk at 50° C. | $Z_6$-$Z_7$ | $Z_1$-$Z_2$ | U-V | $Z_1$+ | $Z_6$-$Z_7$ | U-V |
| 2 wk at R.T. | | | No crystals | | | |

EXAMPLE 6

BEDCy was blended with Prepolymer 1 and Prepolymer 2 described in Example 5. The blends were poured into molds and cured, and the physical properties were determined using the procedure described in Example 3.

BEDCy was also blended with BADCy, METHYLCy and the diglycidyl ether of Bisphenol A having an epoxide equivalent weight of 185. Castings were also prepared from this blend and the physical properties were determined.

The physical properties of the castings are listed in the following table:

| Components | A | B | C |
| --- | --- | --- | --- |
| BEDCy | 60 | 50 | 70 |
| PREPOLYMER 1 | | 50 | |
| PREPOLYMER 2 | 40 | | |
| BADCy | | | 15 |
| METHYLCy | | | 15 |
| DGE | | | 15 |
| Nonyl Phenol | 2.0 | 2.0 | 4.0 |
| Cu Napthenate, 8% | | | 0.31 |
| Zn Napthenate, 8% | 0.15 | 0.15 | |
| Cure Schedule: | | | |
| Gel Temp. | 220° F. | 220° F. | 220° F. |
| @ 350° F. | 1 hr. | 1 hr. | 1 hr. |
| @ 410° F. | 1 hr. | 1 hr. | 1 hr. |
| @ 482° F. | 2 hrs. | 2 hrs. | 2 hrs. |
| Minutes to Gel | 90 | 85 | 20 |
| HDT (°C.) Dry | 195 | 202 | 178 |
| Wet* | 159 | 176 | 145 |
| % H$_2$O Abs.* | 1.62 | 1.64 | 1.46 |
| Flexure Strength (psi) Dry @ R.T. | 25,200 | 22,800 | 27,200 |
| Flexure Modulus (10$^6$ psi) Dry @ R.T. | 0.44 | 0.43 | 0.46 |
| Flexure Strain (%) Dry @ R.T. | 8.05 | 6.36 | 8.94 |
| Flexure Strength (psi) Wet at 180° F.** | 14,900 | 16,500 | 13,400 |
| Flexure Modulus (10$^6$ psi) Wet at 180° F.** | 0.40 | 0.39 | |
| Flexure Strain (%) Wet at 180° F.** | >12.0 | 11.55 | >12.00 |

*Test bars conditioned 64 hours at 200° F. and >95 percent R.H.
**Flexure bars conditioned 48 hours in boiling water prior to testing The principles, preferred embodiments and modes of operation of the present invention have been described in the foregoing specification. The invention which is intended to be protected herein, however, is not to be construed as limited to the particular forms disclosed, since these are to be regarded as illustrating rather than restrictive. Variations and changes may be made by those skilled in the art without departing from the spirit of the invention.

I claim:

1. A curable composition comprising a blend of:
   (a) a dicyanate ester of a dihydric phenol having the formula:

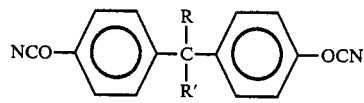

wherein R and R' are difference and wherein R is H or $C_1$ to $C_3$ alkyl and R' is $C_1$ to $C_4$ alkyl, and
   (b) a prepolymer of dicyanate esters of dihydric phenols different from the dicyanate ester of (a) wherein about 5 to about 50 percent of the cyanate functional groups are cyclotrimerized, wherein (a) and (b) are present in the amount of about 1 to about 99 parts by weight of (a) and about 99 to about 1 parts by weight of (b), the total weight being 100 parts.

2. The composition of claim 1 wherein R is hydrogen and R' is methyl.

3. The composition of claim 1 wherein R is methyl and R' is ethyl.

4. The composition of claim 1 wherein the prepolymer is a homopolymer of a dicyanate ester of dihydric phenol.

5. The composition of claim 1 wherein the prepolymer is a copolymer of at least two different dicyanate esters of dihydric phenols.

6. The composition of claim 4 wherein the prepolymer is a prepolymer of di(cyanatophenyl) ether.

7. The composition of claim 4 wherein the prepolymer is a prepolymer of bis(4-cyanatophenyl)-2,2-propane.

8. The composition of claim 4 wherein the prepolymer is a prepolymer of bis(4-cyanato-3,5-dimethylphenyl) methane.

9. The composition of claim 5 wherein the prepolymer is a co-polymer of bis(4-cyanatophenyl)-2,2-propane and bis(4-cyanato-3,5-dimethylphenyl) methane.

10. A curable composition comprising a blend of:
    (a) a dicyanate ester of a dihydric phenol having the formula:

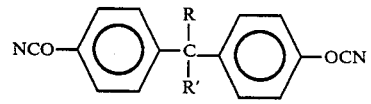

wherein R and R' are different and wherein R is H or $C_1$ to $C_3$ alkyl and R' is $C_1$ to $C_4$ alkyl, and
    (b) a prepolymer of dicyanate esters of dihydric phenols different from the dicyanate ester of (a) wherein about 5 to about 50 percent of the cyanate functional groups are cyclotrimerized, wherein (a) and (b) are present in the amount of about 5 to about 80 parts by weight of (a) and about 95 to about 20 parts by weight of (b), the total weight being 100 parts.

11. The composition of claim 10 wherein R is methyl and R' is ethyl.

12. The composition of claim 10 wherein R is H and R' is methyl.

13. The composition of claim 10 wherein about 15 to about 40 percent of the cyanate functional groups are cyclotrimerized.

14. The composition of claim 13 wherein the prepolymer is a homopolymer of a dicyanate ester of a dihydric phenol.

15. The composition of claim 14 wherein the prepolymer is a prepolymer of bis(4-cyanatophenyl)-2,2-propane.

16. The composition of claim 14 wherein the prepolymer is a prepolymer of bis(4-cyanato-3,5-dimethylphenyl) methane.

17. The composition of claim 14 wherein the prepolymer is a prepolymer of di(cyanatophenyl)ether.

18. The composition of claim 10 wherein the prepolymer is a copolymer of at least two different dicyanate esters of dihydric phenols.

19. The composition of claim 18 wherein the prepolymer is a co-prepolymer of bis(4-cyanatophenyl)-2,2-propane and bis(4-cyanato-3,5-dimethylphenyl) methane.

* * * * *